(12) United States Patent
Sun et al.

(10) Patent No.: US 11,078,150 B2
(45) Date of Patent: Aug. 3, 2021

(54) PREPARATION METHOD FOR CHLOROPHENOXYCARBOXYLATE

(71) Applicant: SHANDONG RAINBOW BIOTECH CO., LTD., Shandong (CN)

(72) Inventors: Guoqing Sun, Shandong (CN); Yongsheng Hou, Shandong (CN); Liguo Zhang, Shandong (CN); Zhilong Chi, Shandong (CN); Yishan Hu, Shandong (CN)

(73) Assignee: SHANDONG RAINBOW BIOTECH CO., LTD., Shandong (CN)

( * ) Notice: Subject to any disclaimer, the term of this patent is extended or adjusted under 35 U.S.C. 154(b) by 0 days.

(21) Appl. No.: 16/979,541

(22) PCT Filed: Feb. 27, 2019

(86) PCT No.: PCT/CN2019/076287
§ 371 (c)(1),
(2) Date: Sep. 10, 2020

(87) PCT Pub. No.: WO2019/179291
PCT Pub. Date: Sep. 26, 2019

(65) Prior Publication Data
US 2021/0002201 A1   Jan. 7, 2021

(30) Foreign Application Priority Data

Mar. 19, 2018 (CN) .......................... 201810226024.7

(51) Int. Cl.
*C07C 67/307* (2006.01)
*C07C 51/363* (2006.01)
*B01J 31/02* (2006.01)

(52) U.S. Cl.
CPC ......... *C07C 67/307* (2013.01); *B01J 31/0218* (2013.01); *C07C 51/363* (2013.01)

(58) Field of Classification Search
CPC ..... C07C 51/363; C07C 67/307; C07C 39/00; C07C 69/635; C07C 17/35; B01J 31/0218
See application file for complete search history.

(56) References Cited

U.S. PATENT DOCUMENTS

| | | | |
|---|---|---|---|
| 4,326,882 A * | 4/1982 | Richter | ................... C07C 59/70 560/62 |
| 4,515,985 A | 5/1985 | Husslein et al. | |
| 2010/0179286 A1 | 7/2010 | Oda et al. | |

FOREIGN PATENT DOCUMENTS

| | | | | |
|---|---|---|---|---|
| CN | 102336654 A * | 2/2012 | ........... | C07C 51/363 |
| CN | 102336654 A | 2/2012 | | |

(Continued)

OTHER PUBLICATIONS

CN 103772200, Tian Xiaohong et al., Preparation method for isooctyl (2,4-dichlorophenoxy) acetate, English translation, 6 pages (Year: 2014).*

(Continued)

*Primary Examiner* — Yate' K Cutliff
(74) *Attorney, Agent, or Firm* — Yue (Robert) Xu; Apex Attorneys at Law, LLP

(57) ABSTRACT

Provided is a method for producing a chlorophenoxycarboxylate, comprising the following steps of: a phenoxycarboxylate under actions of a catalyst A and a catalyst B performing a selective chlorination of a chlorinating agent at a 2-position and/or a 4-position to obtain the chlorophenoxycarboxylate; the catalyst A is a Lewis acid; and the catalyst B has the following structure: $R_1'$—S—$R_2'$. The present disclosure redesigns the process route, and finely screens the catalyst and the chlorinating agent, thereby effectively improving the chlorination selectivity while avoiding the loss of the active ingredient, and the content of (Continued)

the obtained chlorophenoxycarboxylate can reach more than 98.5%, and the yield can reach more than 99%.

10 Claims, 1 Drawing Sheet

(56) References Cited

FOREIGN PATENT DOCUMENTS

| CN | 103772200 A | * | 5/2014 | ........... C07C 67/712 |
| --- | --- | --- | --- | --- |
| CN | 106892808 A | * | 6/2017 | ............. C07C 51/02 |
| CN | 108947840 A | * | 12/2018 | ........... C07C 67/287 |
| EP | 0055357 B1 | | 1/1984 | |
| WO | 2009001670 A1 | | 12/2008 | |

OTHER PUBLICATIONS

CN 102336654, Jianguo Han, et al., Chloration method for phenoxyacetic acid andderivatives thereof, English translation, 9 pages (Year: 2012).*
CN 108947840, Hu Yishan, et al., Preparatin method for chlorophenoxycarboxylate, English translation, 10 pages (Year: 2018).*
CN 106892808, Sun Guoqing, et al., Method for preparing 2,4-dichlorphenoxyacetic acid, English translation, 9 pages (Year: 2017).*
First Examination Report dated Nov. 27, 2020 for Indian patent application No. 202017035432, 3 pages.

* cited by examiner

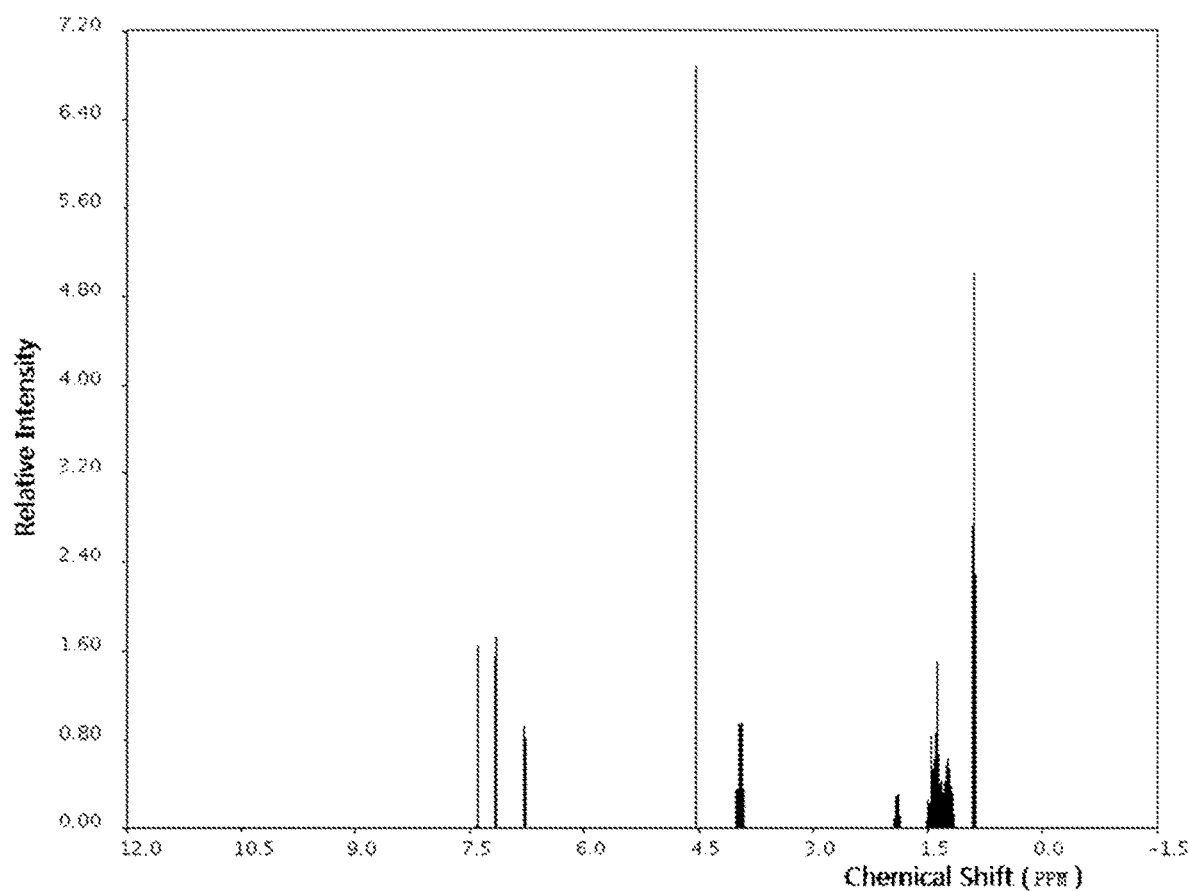

PREPARATION METHOD FOR CHLOROPHENOXYCARBOXYLATE

CROSS REFERENCE TO RELATED APPLICATIONS

This application is the nation phase of International Application No. PCT/CN2019/076287, titled "PREPARATION METHOD FOR CHLOROPHENOXYCARBOXYLATE", filed on Feb. 27, 2019, which claims the priority of Chinese Patent Application No. 201810226024.7, filed on Mar. 19, 2018, filed with China National Intellectual Property Administration, and titled with "PREPARATION METHOD FOR CHLOROPHENOXYCARBOXYLATE", and the disclosures of which are hereby incorporated by reference.

FIELD

The present disclosure relates to the field of herbicide synthesis, in particular to a method for producing a chlorophenoxycarboxylate.

BACKGROUND

Currently, the method for producing a chlorophenoxycarboxylate mainly comprises the following steps.

1) Use a phenol as a main raw material, a chlorophenol is obtained by chlorination. The obtained chlorophenol produced has an extremely unpleasant pungent odor, resulting in a very poor manufacturing condition and poor chlorination selectivity.

2) Perform condensation reaction between chlorophenol and a chlorocarboxylic acid under alkaline condition, and the reaction solution is acidified and filtered to obtain a wet material of chlorophenoxycarboxylic acid, which is dried to obtain a chlorophenoxycarboxylic acid. In this step, during the condensation process, dichlorophenol or polychlorophenol in the chlorophenol will undergo condensation reaction between these two molecules, producing a highly toxic substance—dioxins, which is extremely difficult to be degraded, and the produced chlorophenoxycarboxylic acid also contains dioxins, which pose a great risk to the health of the environment and production personnel.

3) Use the chlorophenoxycarboxylic acid and alcohol as raw materials, the esterification reaction is carried out under the effect of a catalyst, and an organic solvent is used for dehydration by azeotropic distillation during the reaction; and after the completion of the reaction, the resultant is wash with water and the solvent is removed to obtain a chlorophenoxycarboxylate.

In this step, dioxins contained in the chlorophenoxycarboxylic acid enter the chlorophenoxycarboxylate and then enter the plants, air, soil and water sources with the use of the chlorophenoxycarboxylate, causing more serious environmental hazards along with the enrichment by the food chain.

The above method has poor chlorination selectivity, and the post-treatment process causes loss of active ingredients, and the yield of the product is low. At the same time, when a chlorophenoxycarboxylic acid is produced by chlorination reaction and condensation reaction using phenol as a raw material, it will produce a large amount of wastewater containing hydroxy carboxylic acid and salt waste, and a large amount of hazardous waste containing chlorophenols and chlorophenoxycarboxylic acids, resulting in huge pressure on waste disposal and high processing cost.

The available synthesis processes of chlorophenoxycarboxylic acids and esters thereof are very backward, and as worldwide environmental awareness and environmental standards increase constantly, the old and backward technology has seriously restricted the benign and sustainable development of the synthesis of chlorophenoxycarboxylic acids and esters thereof. It is extremely urgent to develop an advanced synthetic process.

SUMMARY

In view of this, the technical problem to be solved in the present disclosure is to provide a method for producing a chlorophenoxycarboxylate, which is efficient and environmentally friendly.

In order to solve above technical problem, the present disclosure provides a method for producing a chlorophenoxycarboxylate, comprising:

subjecting a phenoxycarboxylate to a selective chlorination reaction at 2-position and/or 4-position with a chlorinating agent under effect of a catalyst A and a catalyst B to obtain a chlorophenoxycarboxylate;

the catalyst A is a Lewis acid; and the catalyst B has a structure of:

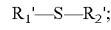

wherein, $R_1'$ and $R_2'$ are independently selected from the group consisting of H, C1~C4 alkyl, phenyl and substituted phenyl, the substituent of the substituted phenyl is one or more selected from the group consisting of C1~C4 alkyl, halogen, hydroxyl, nitro, amino and cyano; and the total number of carbon atoms of $R_1'$ and $R_2'$ is 4~22.

In the present disclosure, the chlorophenoxycarboxylate has a structure represented by any one of formulas I to IV:

formula I

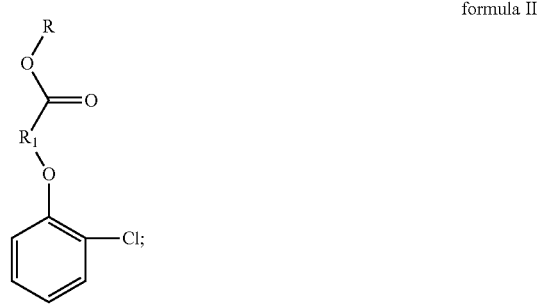

formula II

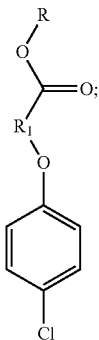

formula III

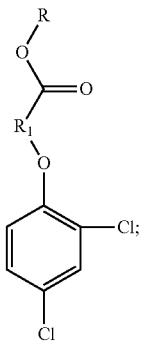

formula V

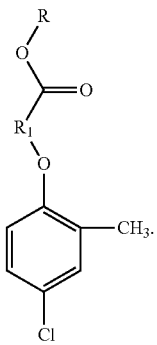

formula VI

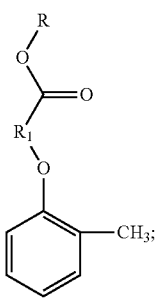

formula IV wherein, $R_1$ is preferably C1~C3 alkylene, further preferably methylene (—CH2-), methyl methylene (—CH(CH3)-), ethylidene(—CH2-CH2-) or propylidene(—CH2-CH2-CH2-).

R is C1~C10 alkyl or C3~C10 cycloalkyl, more preferably C1~C8 alkyl or C3~C8 cycloalkyl, and further preferably methyl, ethyl, propyl, isopropyl, n-butyl, isobutyl, isooctyl or cyclohexyl.

The corresponding products have the following structures:

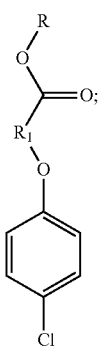

formula III

The catalyst A is a Lewis acid, and preferably is one or more selected from the group consisting of $SnCl_4$, $MgCl_2$, $FeCl_3$, $AlCl_3$, $BF_3$, $ZnCl_2$, $TiCl_4$, $SbF_5$, $Al_2O_3$, $Fe_2O_3$, $TiO_2$, $Pb(OAc)_2$, $Zn(OAc)_2$, and $Al_2O(OAc)_4$; more preferably is one or more selected from the group consisting of $MgCl_2$, $FeCl_3$, $ZnCl_2$, $SbF_5$, $TiO_2$, and $Pb(OAc)_2$; and further preferably is one or more selected from the group consisting of $FeCl_3$, $TiO_2$, and $Pb(OAc)_2$.

More preferably, the catalyst A is a supported catalyst. The supported catalyst is preferably a catalyst supported on silica gel by an impregnation method, and the supported catalyst A preferably has a loading ratio of 10% to 20%.

The catalyst B has the following structure:

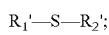

wherein, $R_1'$ and $R_2'$ are independently preferably selected from the group consisting of H, C1~C4 alkyl, phenyl and substituted phenyl, and more preferably selected from the group consisting of H, methyl, ethyl, propyl, isopropyl, n-butyl, isobutyl, tert-butyl, phenyl and substituted phenyl. The total number of carbon atoms of $R_1'$ and $R_2'$ is 4~22.

The substituent of the substituted phenyl is preferably one or more selected from the group consisting of C1~C4 alkyl, halogen, hydroxyl, nitro, amino, and cyano; more preferably one or more selected from the group consisting of methyl, ethyl, propyl, isopropyl, n-butyl, isobutyl, tert-butyl, Cl, Br, and OH.

The catalyst B is more preferably one or more selected from the group consisting of 2-methylthio-2-methylpropane, di-tert-butyl sulfide, 2-mercarpto-2-methylpropane, diphenyl sulfide, 4,4'-dichloro diphenyl sulfide, 2-methyl diphenyl sulfide, 2,4,6-trimethyl diphenyl sulfide, and 4,4'-thio-bis(6-tert-butyl-3-methyl phenol); more preferably one or more selected from the group consisting of di-tert-butyl sulfide, 2,4,6-trimethyl diphenyl sulfide, and 4,4'-thio-bis(6-tert-butyl-3-methyl phenol).

Further preferably, the catalyst B is a supported catalyst. The supported catalyst is preferably a catalyst supported on silica gel by an impregnation method, and the supported catalyst B preferably has a loading ratio of 5% to 15%.

When the catalyst A and the catalyst B are both supported catalysts, the chlorination has a higher selectivity. Particularly, when the catalyst A and the catalyst B are both supported catalysts, the catalyst A and the catalyst B are fixed in a reaction device, enabling the selective chlorination to be carried out in a continuous mode without the need for distillation separation of the reaction product and the catalysts, which greatly improves the productivity of the device and improves the efficiency of use of the catalyst, while saves a lot of energy.

The amount of the catalyst A preferably is 0.05%~1.0% the weight of phenoxycarboxylate, more preferably 0.25%~1.0%, and further preferably 0.5%~1.0%. When the catalyst A is a supported catalyst, the active ingredient in the supported catalyst is used in an amount of 0.05%~1.0% the weight of the phenoxycarboxylate, preferably 0.25%~1.0%, more preferably 0.5%~1.0%. Here, the active ingredient in the supported catalyst means the catalyst A supported on the carrier, and the amount of the active ingredient of the catalyst A=the amount of the supported catalyst A used×the loading ratio.

The amount of the catalyst B is 0.05~1.0% the weight of phenoxycarboxylate, more preferably 0.2%~0.8%, and further preferably 0.3%~0.5%. When the catalyst B is a supported catalyst, the active ingredient in the supported catalyst is used in an amount of 0.05%~1.0% the weight of the phenoxycarboxylate, preferably 0.2%~0.8%, more preferably 0.3%~0.5%. Here, the active ingredient in the supported catalyst means the catalyst B supported on the carrier, and the amount of the active ingredient of the catalyst B=the amount of the supported catalyst B used×the loading ratio.

Using too small amount of the catalyst A is not recommended, which will otherwise results in a great reduce in the chlorination selectivity, but using excessive amount will increase the difficulty of product separation in addition to diseconomy. Using too small amount of the catalyst B is not recommended, which will otherwise results in nonoccurrence or slow proceeding of the reaction, using excessive amount will not only be uneconomic but also results in a decrease in selectivity, and will increase the difficulty of product separation at the same time.

The chlorinating agent may be a general chlorinating agent for phenol chlorination, preferably chlorine gas, thionyl chloride or sulfuryl chloride, more preferably chlorine gas or sulfuryl chloride.

The 2-position and/or 4-position selective chlorination reaction refer to a mono-substitution reaction at 2-position, a mono-substitution reaction at 4-position, or a double substitution reaction at 2-position and 4-position.

When the selective chlorination reaction is a mono-substitution reaction at 2- or 4-position, such as the phenoxycarboxylate shown in Formula I to Formula IV, the mole ratio of the phenoxycarboxylate to the chlorinating agent is preferably 1: (0.98 to 1.2), more preferably 1: (1 to 1.1), even more preferably 1: (1.01 to 1.03).

When the selective chlorination reaction is a double substitution reaction at 2-position and 4-position, such as the phenoxycarboxylate shown in Formula I (product: 2,4-dichlorophenoxycarboxylate), the mole ratio of the phenoxycarboxylate to the chlorinating agent is preferably 1: (1.98 to 2.4), more preferably 1: (2 to 2.2), even more preferably 1: (2.02 to 2.06).

Using too small amount of the chlorinating agent is not recommended, which will otherwise make more raw materials cannot be transformed, but using excessive amount will result in too much formation of superchlorination product, which is not good for the reaction.

The temperature of the selective chlorination reaction is preferably −20 to 100° C., more preferably −20 to 60° C., even more preferably −20 to 20° C. The duration of the reaction is preferably 0.2 to 1 hour.

The reaction temperature can maintain high reaction activity and chlorination selectivity at the same time.

After the completion of the selective chlorination reaction, the method further comprises performing distillation under a reduced pressure, and collecting a fraction of corresponding boiling point range to obtain a chlorophenoxycarboxylate.

When the catalyst is a supported catalyst, the chlorophenoxycarboxylate is directly obtained by filtration. Therefore, the present disclosure has three outstanding advantages when using the supported catalysts A and B. First, the catalyst and the product are easily separated; secondly, the catalyst can be recycled for reuse; and thirdly, it facilitates the continuous operation, improves the utilization efficiency of the catalyst, and improves the productivity of the device and saves a lot of energy.

By re-designing the process route, screening the catalyst and the chlorinating agent, Lewis acid and the specific catalyst are used together, which makes the chlorination selectivity reach more than 99.5%, and the untransformed raw material content in the obtained reactant is less than 0.1%, the total content of by-products of the reaction is less than 0.5%.

The impurities and impurity contents of the chlorophenoxycarboxylate produced by the present disclosure are shown in Table 1.

TABLE 1

Summary of Impurities and Impurity Contents of the Chlorophenoxycarboxylate Produced by the Present Disclosure

| | | Mole Ratio of each component in the Chlorophenoxycarboxylate | | | | |
|---|---|---|---|---|---|---|
| Substance | Target Product | Untransformed Substance | Target Product | By-product 1 | By-product 2 | Catalyst B and chloro compounds thereof |
| Formula I | Formula III | Phenoxycarboxylate <0.1 | P-chlorophenoxycarboxylate ≥99.4 | O-chlorophenoxycarboxylate <0.1 | 2,4-dichlorophenoxycarboxylate <0.2 | ≤0.2 |

TABLE 1-continued

Summary of Impurities and Impurity Contents of the Chlorophenoxycarboxylate Produced by the Present Disclosure Mole Ratio of each component in the Chlorophenoxycarboxylate

| Substance | Target Product | Untransformed Substance | Target Product | By-product 1 | By-product 2 | Catalyst B and chloro compounds thereof |
|---|---|---|---|---|---|---|
| Formula I | Formula V | P-chlorophenoxycarboxylate <0.1 | 2,4-dichlorophenoxycarboxylate ≥99.3 | 2,6-dichlorophenoxycarboxylate <0.1 | 2,4,6-trichlorophenoxycarboxylate <0.3 | ≤0.2 |
| Formula II | Formula V | O-chlorophenoxycarboxylate <0.1 | 2,4-dichlorophenoxycarboxylate ≥99.4 | 2,6-dichlorophenoxycarboxylate <0.2 | 2,4,6-trichlorophenoxycarboxylate <0.1 | ≤0.2 |
| Formula III | Formula V | P-chlorophenoxycarboxylate <0.1 | 2,4-dichlorophenoxycarboxylate ≥99.3 | 2,6-dichlorophenoxycarboxylate <0.1 | 2,4,6-trichlorophenoxycarboxylate <0.2 | ≤0.2 |
| Formula IV | Formula VI | O-methylphenoxycarboxylate <0.1 | 4-chloro-2-methylphenoxycarboxylate ≥99.3 | 2-chloro-6-methylphenoxycarboxylate <0.1 | 2,4-dichloro-6-methylpnenoxycarboxylate <0.3 | ≤0.2 |

The chlorophenoxycarboxylate produced by the present disclosure can be directly used as an herbicide product, or an auxiliary agent can be directly added to prepare various herbicide preparations.

Compared to the conventional art, the present disclosure provides a method for producing a chlorophenoxycarboxylate, comprising: subjecting a phenoxycarboxylate to a selective chlorination reaction at 2-position and/or 4-position with a chlorinating agent under effect of a catalyst A and a catalyst B to obtain a chlorophenoxycarboxylate; the catalyst A is a Lewis acid; and the catalyst B has a structure of: $R_1'$—S—$R_2'$. Catalysts A and B are more effective when present in the supported form.

The present disclosure uses phenoxycarboxylate as a raw material to synthesize chlorophenoxycarboxylate by selective chlorination under the effect of a catalyst, thereby effectively improving chlorination selectivity while avoiding loss of active ingredients. The content of the obtained chlorophenoxycarboxylate can reach 98.5% or more, and the yield can reach 99% or more. Compared to the available synthesis technique, the synthetic route has been greatly simplified, the generation and use of chlorophenol with unpleasant odor has been effectively avoided, and the production of highly toxic dioxins has been fundamentally eliminated, and product quality and manufacturing condition have been greatly improved. Mother liquor containing active ingredient is not produced, thereby effectively avoiding the loss of the active ingredient, improving the yield of the product, and at the same time reducing the energy consumption due to the simplification of the process flow, effectively preventing the production of high COD and high salt wastewater, the output of the wastes has been greatly reduced.

BRIEF DESCRIPTION OF DRAWINGS

FIG. 1 is the proton nuclear magnetic resonance spectrum of the isooctyl 2,4-dichlorophenoxyacetate obtained in Example 8.

DETAILED DESCRIPTION

In order to further illustrate the present disclosure, the method for producing a chlorophenoxycarboxylate provided by the present disclosure will be described in detail below with reference to the examples.

Example 1

167.87 g of 99% methyl phenoxyacetate (1 mol), 1.43 g of 99% stannic chloride and 1.09 g of 99% di-tert-butyl sulfide were sequentially added to a 500 ml four-neck flask. 237.92 g of 99% thionyl chloride (1.98 mol) was added dropwise at 20° C., and then the reaction was carried out at the same temperature for 30 minutes. The resultant was distilled under a pressure of 1 kpa, and the fraction of 140-150° C. was collected to give 236.07 g of methyl (2,4-dichlorophenoxy)acetate. The content was 98.9%, and the yield was 99.32% based on methyl phenoxyacetate.

After testing, the impurities include: methyl 4-chlorophenoxy acetate content 0.07%, 2,6-dichloro methyl phenoxy acetate content 0.03%, methyl 2,4,6-trichlorophenoxyacetate content 0.19%, and di-tert-butyl sulfide content 0.011%.

Comparative Example 1

167.87 g of 99% methyl phenoxyacetate (1 mol) and 2 g of 99% stannic chloride were sequentially added to a 500 ml four-neck flask. 237.92 g of 99% thionyl chloride (1.98 mol) was added dropwise at 20° C., and then the reaction was carried out at the same temperature for 30 minutes. The resultant was distilled under a pressure of 1 kpa, and the fraction of 140-150° C. was collected to give 215.52 g of methyl (2,4-dichlorophenoxy)acetate. The content was 98.7%, and the yield was 90.49% based on methyl phenoxyacetate.

Comparative Example 2

167.87 g of 99% methyl phenoxyacetate (1 mol) and 2 g of 99% di-tert-butyl sulfide were sequentially added to a 500 ml four-neck flask. 237.92 g of 99% thionyl chloride (1.98 mol) was added dropwise at 20° C., and then the reaction was carried out at the same temperature for 30 minutes. The resultant was distilled under a pressure of 1 kpa, and the fraction of 140-150° C. was collected to give 193.95 g of methyl (2,4-dichlorophenoxy)acetate. The content was 98.5%, and the yield was 81.27% based on methyl phenoxyacetate.

Example 2

210.38 g of 99% n-butyl phenoxyacetate (1 mol), 1.58 g of 99% zinc chloride and 2.10 g of 99% 2,4,6-trimethyl diphenyl sulfide were sequentially added to a 500 ml four-neck flask. 77.35 g of 99% chlorine gas (1.08 mol) was pumped into the flask at −20° C., and then the reaction was carried out at the same temperature for 30 minutes. The resultant was distilled under a pressure of 1 kpa, and the fraction of 150-160° C. was collected to give 243.63 g of n-butyl (4-chlorophenoxy)acetate. The content was 98.7%, and the yield was 99.07% based on n-butyl phenoxyacetate.

Example 3

196.21 g of 99% methyl phenoxybutyrate (1 mol), 0.29 g of 99% ferric chloride and 0.69 g of 99% 4,4'-thio-bis(6-tert-butyl-3-methyl phenol) were sequentially added to a 500 ml four-neck flask. 275.39 g of 99% sulfuryl chloride (2.02 mol) was added dropwise at 30° C., and then the reaction was carried out at the same temperature for 30 minutes. The resultant was distilled under a pressure of 1 kpa, and the fraction of 150-160° C. was collected to give 263.63 g of methyl (2,4-dichlorophenoxy)butyrate. The content was 99.0%, and the yield was 99.19% based on methyl phenoxybutyrate.

Example 4

196.21 g of 99% ethyl 2-phenoxypropionate (1 mol), 1.08 g of 99% titanium tetrachloride and 0.88 g of 99% 4,4'-dichloro diphenyl sulfide were sequentially added to a 500 ml four-neck flask. 78.78 g of 99% chlorine gas (1.1 mol) was pumped into the flask at 0° C., and then the reaction was carried out at the same temperature for 30 minutes. The resultant was distilled under a pressure of 1 kpa, and the fraction of 145-155° C. was collected to give 228.99 g of ethyl 2-(4-chlorophenoxy)propionate. The content was 99.2%, and the yield was 99.33% based on ethyl 2-phenoxypropionate.

Example 5

273.52 g of 99% isobutyl 2-chlorophenoxybutyrate (1 mol), 0.14 g of 99% aluminum chloride and 0.41 g of 99% 2-methylthio-2-methylpropane were sequentially added to a 500 ml four-neck flask. 85.94 g of 99% chlorine gas (1.2 mol) was pumped into the flask at 50° C., and then the reaction was carried out at the same temperature for 30 minutes. The resultant was distilled under a pressure of 1 kpa, and the fraction of 160-170° C. was collected to give 305.25 g of isobutyl (2,4-dichlorophenoxy)butyrate. The content was 99.4%, and the yield was 99.41% based on isobutyl 2-chlorophenoxybutyrate.

Example 6

196.21 g of 99% ethyl 2-phenoxypropionate (1 mol), 0.69 g of 99% titanium dioxide and 1.08 g of 99% 4,4'-dichloro diphenyl sulfide were sequentially added to a 500 ml four-neck flask. 280.85 g of 99% sulfuryl chloride (2.06 mol) was added dropwise at 60° C., and then the reaction was carried out at the same temperature for 30 minutes. The resultant was distilled under a pressure of 1 kpa, and the fraction of 150-160° C. was collected to give 263.02 g of ethyl 2-(2,4-dichlorophenoxy)propionate. The content was 99.3%, and the yield was 99.26% based on ethyl 2-phenoxypropionate.

Example 7

259.34 g of 99% n-butyl 2-(4-chlorophenoxy)propionate (1 mol), 0.65 g of 99% lead acetate and 0.13 g of 99% 2-mercarpto-2-methylpropane were sequentially added to a 500 ml four-neck flask. 118.96 g of thionyl chloride (0.99 mol) was added dropwise at 40° C., and then the reaction was carried out at the same temperature for 30 minutes. The resultant was distilled under a pressure of 1 kpa, and the fraction of 155-165° C. was collected to give 291.22 g of n-butyl 2-(2,4-dichlorophenoxy)propionate. The content was 99.0%, and the yield was 99.01% based on n-butyl 2-(4-chlorophenoxy)propionate.

Example 8

267.07 g of 99% isooctyl phenoxyacetate (1 mol), 2.67 g of 99% aluminum oxide and 2.27 g of 99% 4,4'-thio-bis(6-tert-butyl-3-methyl phenol) were sequentially added to a 500 ml four-neck flask. 171.88 g of 99% chlorine gas (2.4 mol) was pumped into the flask at 100° C., and then the reaction was carried out at the same temperature for 30 minutes. The resultant was distilled under a pressure of 1 kpa, and the fraction of 175-185° C. was collected to give 333.35 g of isooctyl (2,4-dichlorophenoxy)acetate. The content was 99.1%, and the yield was 99.12% based on isooctyl phenoxyacetate.

The obtained isooctyl (2,4-dichlorophenoxy)acetate was detected by nuclear magnetic resonance, and the result is shown in FIG. 1. FIG. 1 is the proton nuclear magnetic resonance spectrum of isooctyl (2,4-dichlorophenoxy)acetate.

Example 9

30.34 g of a magnesium chloride/silica gel supported catalyst with a loading rate of 20% and 6.07 g of a 2-methyl diphenyl sulfide/silica gel supported catalyst with a loading rate of 5% were respectively added to a three-stage series continuous reactor (100 mL of each volume), and 91.02 g of 99% methyl 2-methylphenoxyacetate (0.5 mol) was added to the first-stage reactor and stirred, and then 68.85 g of 99% sulfuryl chloride (0.505 mol) was added at 100° C. at a constant speed. With the addition of sulfuryl chloride, the material overflowed from the first-stage reactor into the second-stage reactor, and the temperature of the second-stage reactor was controlled to be 100° C. After the addition of sulfuryl chloride, 1729.38 g of 99% methyl 2-methyl phenoxyacetate (9.5 mol) and 1308.15 g of 99% sulfuryl chloride (9.595 mol) were added proportionally at a constant speed. With the addition of the material into the first-stage reactor, the material continuously overflowed into the second-stage reactor and the third-stage reactor. When materials entered the third-stage reactor, the temperature was maintained at 100° C. The reactant finally overflowed the system from the third-stage reactor to give methyl 4-chloro-2-methylphenoxyacetate, while the supported catalysts did not flow out of the system with the materials due to its high density. After all the materials had been added, the temperature was maintained constant for 30 min, the materials in the first, second and third-stage reactors were filtered and combined with the methyl 4-chloro-2-methylphenoxyacetate from the third-stage reactor to give 2146.00 g of methyl 4-chloro-2-methylphenoxyacetate. The content was 99.4%, and the yield was 99.37% based on methyl 2-methylphenoxyacetate.

Example 10

309.59 g of 99% of isooctyl 2-methylphenoxybutyrate (1 mol), 1.55 g of an iron oxide/silica gel supported catalyst having a loading rate of 10%, and 20.67 g of a 2-methylthio-2-methylpropane/silica gel were sequentially added to a 500 ml four-neck flask. 140.42 g of 99% sulfuryl chloride (1.03 mol) was added dropwise at 40° C., and then the reaction was carried out at the same temperature for 30 minutes. The resultant was filtered to give 341.38 g of isooctyl 4-chloro-2-methylphenoxybutyrate. The content was 99.4%, and the yield was 99.53% based on isooctyl 2-methylphenoxybutyrate.

Example 11

21.24 g of a titanium dioxide/silica gel supported catalyst with a loading rate of 15% and 31.86 g of a di-tert-butyl sulfide/silica gel supported catalyst with a loading rate of 10% were respectively added to a three-stage series continuous reactor (100 mL of each volume), and 91.02 g of 99% methyl 2-methylphenoxyacetate (0.5 mol) was added to the first-stage reactor and stirred, and then 68.85 g of 99% sulfuryl chloride (0.505 mol) was added at −20° C. at a constant speed. With the addition of sulfuryl chloride, the material overflowed from the first-stage reactor into the second-stage reactor, and the temperature of the second-stage reactor was controlled to be −20° C. After the addition of sulfuryl chloride, 1729.38 g of 99% methyl 2-methyl phenoxyacetate (9.5 mol) and 1308.15 g of 99% sulfuryl chloride (9.595 mol) were added proportionally at a constant speed. With the addition of the material into the first-stage reactor, the material continuously overflowed into the second-stage reactor and the third-stage reactor. When the materials entered the third-stage reactor, the temperature was maintained at −20° C., and the reactant finally overflowed the system from the third-stage reactor to give methyl 4-chloro-2-methylphenoxyacetate, while the supported catalysts did not flow out of the system with the material due to its high density. After all the materials had been added, the temperature was maintained constant for 30 min, the materials in the first, second and third-stage reactors were filtered and combined with the methyl 4-chloro-2-methylphenoxyacetate from the third-stage reactor to give 2145.14 g of methyl 4-chloro-2-methylphenoxyacetate. The content was 99.1%, and the yield was 99.13% based on methyl 2-methylphenoxyacetate.

As can be seen from the above examples, the method provided by the present disclosure has high yield and purity, and the selectivity of the chlorination reaction is high.

The illustration of the above embodiments is merely to assist in understanding the method of the present disclosure and the core idea thereof. It should be pointed out that a person having ordinary skill in the art can make a number of improvements or modifications to the present disclosure without departing from the principles of the present disclosure, and such improvements and modifications also fall within the scope of protection claimed by the present disclosure.1

The invention claimed is:

1. A method for producing a chlorophenoxycarboxylate, comprising:

subjecting a phenoxycarboxylate to a selective chlorination reaction at 2-position and/or 4-position with a chlorinating agent under effect of a catalyst A and a catalyst B to obtain a chlorophenoxycarboxylate;

wherein, the catalyst A is a Lewis acid; and the catalyst B has a structure of:

wherein, $R_1'$ and $R_2'$ are independently selected from the group consisting of H, C1~C4 alkyl, phenyl and substituted phenyl, the substituent of the substituted phenyl is one or more selected from the group consisting of C1~C4 alkyl, halogen, hydroxyl, nitro, amino and cyano; and the total number of carbon atoms of $R_1'$ and $R_2'$ is 4~22.

2. The method according to claim 1, wherein the phenoxycarboxylate has a structure represented by any one of formulas I to IV:

formula I

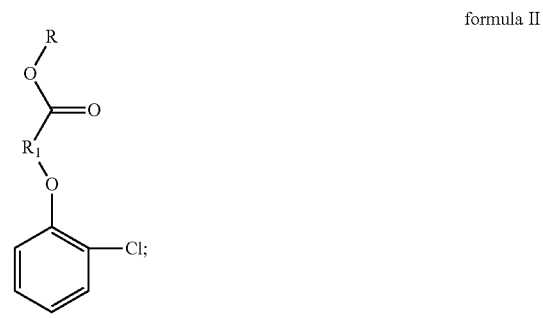

formula II

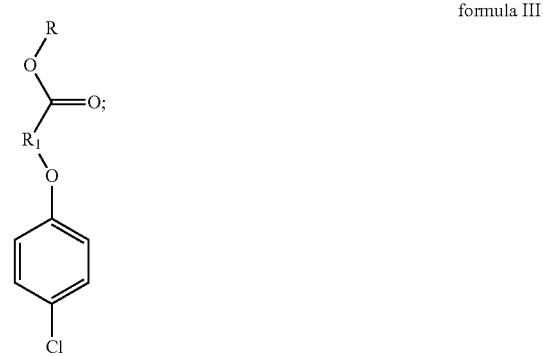

formula III

-continued

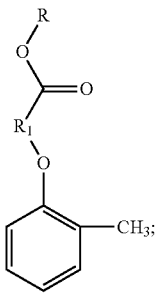

formula IV wherein, $R_1$ is C1~C3 alkylene; and

R is C1~C10 alkyl or C3~C10 cycloalkyl.

3. The method according to claim 2, wherein $R_1$ is selected from the group consisting of —$CH_2$—, —CH($CH_3$)—, —$(CH_2)_2$— and —$(CH_2)_3$—; and R is selected from the group consisting of methyl, ethyl, propyl, isopropyl, n-butyl, isobutyl, isooctyl and cyclohexyl.

4. The method according to claim 1, wherein the catalyst A is one or more selected from the group consisting of $SnCl_4$, $MgCl_2$, $FeCl_3$, $AlCl_3$, $BF_3$, $ZnCl_2$, $TiCl_4$, $SbF_5$, $Al_2O_3$, $Fe_2O_3$, $TiO_2$, $Pb(OAc)_2$, $Zn(OAc)_2$, and $Al_2O(OAc)_4$.

5. The method according to claim 1, wherein the catalyst B is one or more selected from the group consisting of 2-methylthio-2-methylpropane, di-tert-butyl sulfide, 2-mercarpto-2-methylpropane, diphenyl sulfide, 4,4'-dichloro diphenyl sulfide, 2-methyl diphenyl sulfide, 2,4,6-trimethyl diphenyl sulfide, and 4,4'-thio-bis(6-tert-butyl-3-methyl phenol).

6. The method according to claim 1, wherein the amount of the catalyst A is 0.05% to 1.0% the weight of the phenoxycarboxylate; and the amount of the catalyst B is 0.05% to 1.0% the weight of the phenoxycarboxylate.

7. The method according to claim 1, wherein the reaction temperature is −20~100° C.

8. The method according to claim 1, after the completion of the selective chlorination reaction, further comprising performing distillation under a reduced pressure to obtain the chlorophenoxycarboxylate.

9. The method according to claim 1, wherein the catalyst A and/or the catalyst B is a supported catalyst.

10. The method according to claim 9, after the completion of the selective chlorination reaction, further comprising directly performing filtration to obtain the chlorophenoxycarboxylate.

* * * * *